United States Patent [19]

Mochida et al.

[11] 4,315,003
[45] Feb. 9, 1982

[54] COMPOSITIONS CONTAINING AZO COMPOUNDS AND USE THEREOF FOR THERAPEUTIC TREATMENT

[75] Inventors: Ei Mochida, Tokyo; Yasuo Suzuki, Kawaguchi; Haruo Onishi, Funabashi; Hiroshi Kosuzume, Yokohama, all of Japan

[73] Assignee: Mochida Seiyaku Kabushiki Kaisha, Japan

[21] Appl. No.: 173,358

[22] Filed: Jul. 29, 1980

[30] Foreign Application Priority Data

Jul. 30, 1979 [JP] Japan ................................. 54-97059

[51] Int. Cl.$^3$ ............................................. A61K 31/655
[52] U.S. Cl. ................................................... 424/226
[58] Field of Search ......................... 424/226; 260/157

[56] References Cited

U.S. PATENT DOCUMENTS

| | | | |
|---|---|---|---|
| 3,102,879 | 9/1963 | Baumann et al. | 260/157 |
| 3,173,907 | 3/1965 | Klingsberg et al. | 260/157 |
| 3,216,995 | 11/1965 | Baumann et al. | 260/157 |
| 3,294,777 | 12/1966 | Hansen et al. | 260/157 |
| 3,357,783 | 12/1967 | Wunderlech et al. | 260/157 X |
| 3,468,871 | 9/1969 | Leverenz et al. | 260/157 X |
| 3,981,885 | 9/1976 | Buchel et al. | 260/157 X |

OTHER PUBLICATIONS

Beilstein, "Handbuch der Organischen Chemie," vol. 24, 2nd Supplement, p. 37 (1954).

*Primary Examiner*—Stanley J. Friedman
*Attorney, Agent, or Firm*—Stevens, Davis, Miller & Mosher

[57] ABSTRACT

The compositions for therapeutic treatment contain as an active ingredient a 2-[(2-methoxyphenyl)-axo]-1H-imidazole derivative of the formula:

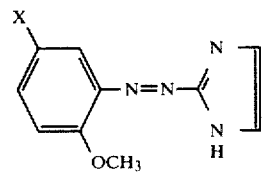

wherein X is hydrogen or halogen, or a pharmaceutically acceptable salt thereof. This compound is effective for the therapeutic treatment of edema, hypotension, cardiac insufficiency and mucosa hyperemia.

6 Claims, No Drawings

COMPOSITIONS CONTAINING AZO COMPOUNDS AND USE THEREOF FOR THERAPEUTIC TREATMENT

BACKGROUND OF THE INVENTION

1. Field of the Invention

The present invention relates to a composition and a use for therapeutic treatment and, more particularly, to a composition containing as an active ingredient and a use of an azo compound for the therapeutic treatment of edema, hypotension, cardiac insufficiency and mucosal hyperemia.

2. Brief Description of Prior Art

Heretofore, there have been applied diuretics to prevent secondary diseases from being caused by excreting accumulated extracellular fluids when edema is caused by the accumulation of water or an electrolyte as a result of the hypofunction and the obstraction of metabolisms in the kidney or the heart.

Vasopressors have also been used to treat the vertigo which often would occur in hypotension with autonomic ataxia.

Furthermore, cardiotonics have also been employed for the treatment of chronic hypofunction of the heart, diseases being caused by the cardiac insufficiency as a cause of the edema and the hypotension.

Among medicines having the hypertensive action, there may be provided a medicine such as phenirephrine having the action of mucosal hyperemia. Accordingly, there is a possibility that, among medicines having consolidated pharmacological effects against edema, hypotension or cardiac insufficiency, a medicine can be provided which effects a sufferring identical with or similar to the above-mentioned mucosa hyperemia. There have been desire and need for the provision of such a therapeutic agent having the combined effects.

SUMMARY OF THE INVENTION

Accordingly, the object of the present invention is to provide a composition pharmaceutically effective for use in the therapeutic treatment of edema, hypotension, and cardiac insufficiency as well as mucosal hyperemia.

Another object of the present invention is to provide a use for such therapeutic treatment of a therapeutic agent or a compound having the combined effects against edema, hypotension, and cardiac insufficiency as well as mucosal hyperemia.

Other objects and advantages and features of the present invention will become apparent during the course of the description which follows.

DETAILED DESCRIPTION OF THE INVENTION

The compound to be used for these purposes in accordance with the present invention is an azo compound that may be represented by the formula:

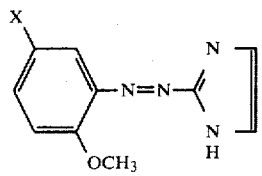

wherein X is hydrogen or halogen. A pharmaceutically acceptable salt thereof also may be used for the purposes intended to be achieved in accordance with the present invention.

The azo compounds may be prepared first by reacting a 2-methoxyaniline derivative with sodium nitrite and hydrochloric acid in an appropriate solvent and then by reacting the resulting diazonium salt with imidazole. The reaction scheme may be represented as follows:

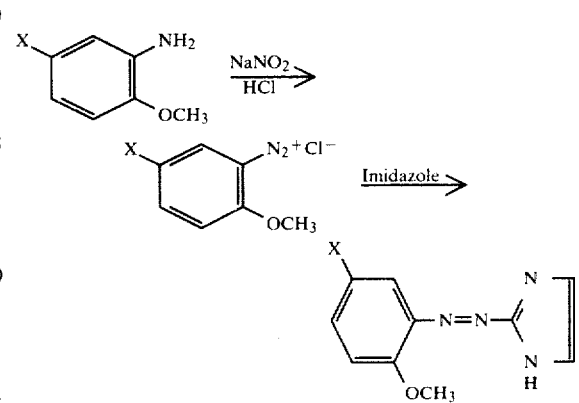

The azo compounds may be conveniently converted into the corresponding pharmaceutically acceptable salts thereof in conventional manner. Illustrative of the pharmaceutically acceptable salts may be, for example, inorganic acid addition salts, e.g., hydrochloride, hydrobromide, hydroiodide, sulfate, nitrate, phosphate or the like, and organic acid addition salts, e.g., acetate, maleate, citrate, tartrate, oxalate, succinate or the like.

An example of preparing the azo compound may be illustrated as follows: To 50 parts by weight of water are added 5.1 parts by weight of 4-chloro-2-aminoanisole and 7.6 parts by weight of 35% hydrochloric acid, and a mixture of 2.2 parts by weight of sodium nitrate and 15 parts by weight of water is added thereto at 0°–5° C. The resulting mixture is stirred for 1 hour for the completion of diazotation. The first reaction mixture is then added at 0°–5° C. to a solution of 20.4 parts by weight of imidazole, 1.7 parts by weight of sodium hydroxide and 2.5 parts by weight of sodium acetate in 150 parts by weight of water. Stirring of the mixture for 1 hour can allow the diazonium salt to effect the coupling with imidazole, thereby precipitating a yellow-orange product. The product is then filtered, washed with water and then dried at 60° C. to provide 7.6 parts by weight of the crude azo compound. This crude azo compound (7 parts by weight) is recrystallized from n-propylalcohol to provide 7.6 parts by weight of pure 2-[(2-methoxy-5-chlorophenyl)azo]-1H-imidazole, having a melting point of 205° C. (decomposed), when measured in accordance with the designation of the Japanese Pharmacopoeia. It has a maximum ultraviolet absorption peak ($\lambda_{max}$) at 384 m$\mu$ and its elementary analysis indicates as follows:

|  | C | H | N | Cl |
|---|---|---|---|---|
| Calculated (%) | 50.75 | 3.83 | 23.68 | 14.98 |
| Found (%) | 50.55 | 4.01 | 24.10 | 15.05 |

This compound (hereinafter referred to "Compound A") is a yellow-orange columnar crystalline substance and less soluble in water and hexane and readily soluble in acetone and methanol.

In the same manner as in the above example, the following azo compounds may be prepared:

Compound B:

2-[(2-methoxy-5-fluorophenyl)azo]-1H-imidazole; yellow-orange acicular crystals; m.p. 204° C. (decomposed); $\lambda_{max} = 388$ m$\mu$; Elementary analysis: Calculated (%) C 54.55, H 4.09 N 25.45, F 8.64, Found (%) C 54.60, H 4.12, N 25.58, F 8.69; less soluble in water and hexane and readily soluble in acetone and methanol.

Compound C:

2-[(2-methoxy-5-bromophenyl)azo]-1H-imidazole; yellow-orange acicular crystals; m.p. 224.5 (decomposed); $\lambda_{max} = 387$ m$\mu$; Elementary analysis: Calculated (%) C 42.70, H 3.20, N 19.93, Br 28.44, Found (%) C 42.71, H 3.27, N 19.90, Br 28.39; sparingly soluble in water and hexane and readily soluble in acetone and methanol.

Compound D:

2-[2-methoxy-5-iodophenyl)azo]-1H-imidazole; yellow-orange acicular crystals; m.p. 217.5° C. (decomposed); $\lambda_{max} = 385$ m$\mu$; Elementary analysis: Calculated (%) C 36.59, H 2.74, N 17.07, I 38.69, Found (%) C 36.61, H 2.70, N 17.09, I 38.61; sparingly soluble in water and hexane and readily soluble in acetone and methanol.

Compound E:

2-[(2-methoxyphenyl)azo]-1H-imidazole; yellow columnar crystals; m.p. 152°-153° C.; sparingly soluble in water and hexane and readily soluble in acetone and methanol.

The compositions for therapeutic treatment in accordance with the present invention may contain the azo compound as an active ingredient, which may be used singly or in admixture with each other, and a pharmaceutically acceptable and/or pharmaceologically inert diluent, carrier, base, adjuvant, filler, excipient, colorant, flavoring and/or corrigent. These additives may be one that may be arbitrarily or customarily used for preparing pharmaceutical preparations. The compositions also may be applied usually in the form of orally administrable preparations such as solutions, suspensions, capsules, tablets or powders, of injections for intravenous, intraperetonial or intramuscular administrations, or of tropical administrations such as eye drops, nose drops or suppositories. The compositions especially for application in injections may be stored in the lyophilized form and dissolved in sterilized distilled water for injection use immediately before application. These preparations may contain the azo compound as the active ingredient in a dosage amount ranging generally from 0.01 mg to 1,000 mg, varying depending upon the sex, age or disease symptom of a patient or application. For example, a dosage per day for an adult patient may usually range from about 1 to 1,000 mg for Compounds C, D, and E, and from about 0.5 to 500 mg for Compounds A and B. For tropical applications, for example, Compounds C, D, and E may be used in the range from about 0.05 to 1 mg, and Compounds A and B in the range from about 0.01 to 0.5 mg.

The following examples illustrate the compositions in accordance with the present invention, but should not be construed in any manner as limiting the present invention thereto.

EXAMPLE 1

Capsules

| Ingredients | Amounts (g) |
|---|---|
| Compound E | 125 |
| Lactose | 860 |
| Magnesium stearate | 15 |

The ingredients were homogeneously mixed and filled in No. 3 hard gelatin capsules so as to contain 200 mg each.

EXAMPLE 2

Tablets

| Ingredients | Amounts (g) |
|---|---|
| Compound B | 50 |
| Lactose | 675 |
| Potato starch | 260 |
| Magnesium stearate | 15 |

A homogeneous mixture of Compound B, lactose, and 240 grams of potato starch was added to a 10% potato starch paste which had been previously prepared by using the rest (20 grams) of potato starch and hot water. The resulting mixture was granulated by a conventional wet-type granulating method to provide granules which were then mixture with magnesium stearate and then tabletted by means of a tabletting machine to provide 7.5 mm tablets weighing 200 mg.

EXAMPLE 3

5% Powdery preparation

| Ingredients | Amounts (grams) |
|---|---|
| Compound C | 50 |
| Lactose | 940 |
| Magnesium stearate | 10 |

The ingredients were homogeneously mixed to give a 5% powdery preparation.

EXAMPLE 4

Injectable solutions

One gram of Compound A hydrochloride was dissolved in 2,000 ml of sterilized distilled water for injection use and aseptically filtered with a membrane filter, and filled in glass vials so as to contain 4 ml each. The vials were then subjected to lyophilization and closed to provide lyophilized powdery preparations.

EXAMPLE 5

Suppository

| Ingredients | Amounts (grams) |
|---|---|
| Compound D | 50 |
| Polyethylene glycol 1500 | 200 |
| Polyethylene glycol 4000 | 750 |

Compound D was milled in a mortar to give finely divided powders which were in turn molten to form suppositories.

EXAMPLE 6

Eye drops

| Ingredients | Amounts (grams) |
|---|---|
| Compound A hydrochloride | 0.2 |
| Sodium chloride | 5 |
| Chlorobutanol | 5 |
| Distilled water added to become | 1,000 ml. |

The above first three ingredients were heated to 80° C. and then dissolved in 950 ml of distilled water for injection use. After being allowed to cool, the mixture was adjusted to become 1,000 ml in total and then aseptically filtered with a membrane filter to provide a 0.02% eye drop preparation.

EXAMPLE 7

0.01% Nose drops

| Ingredients | Amounts (grams) |
|---|---|
| Compound B hydrochloride | 0.1 |
| Sodium chloride | 5 |
| Chlorobutanol | 5 |
| Distilled water added to become | 1,000 ml |

The first three ingredients were heated to 80° C. and then dissolved in 950 ml of distilled water. After being left to cool, the mixture was diluted to become 1,000 ml to provide a 0.01% nose drop preparation.

The azo compounds were tested for their pharmacological effects, toxicity, and dosages, and doses.

EXPERIMENT 1

Diuretic Action in Rats

A group of 5 male rats of Wistar strain having each a body weight ranging from 180 to 200 grams was used for each test compound. The rats were fasted overnight and then abstained from water two hours before the administration of the test compound. The test compound was prepared by suspending the compound in a 5% arabic gum-saline solution and administered orally to the rats in the amount of 25 ml per kg. of body weight.

The urine was collected during 5 hours after administration and its volume was measured. The diuretic actions of the test compounds were calculated as the urinary volume of the control group where no test compound was administered being as 100%. The test results are shown in Table 1.

TABLE 1

| Test Compound | Dose, mg/kg | Diuretic Activity, % |
|---|---|---|
| Control | — | 100 |
| Compound A | 0.5 | 133 |
| " | 1.0 | 183 |
| " | 2.0 | 329 |
| Compound B | 1.0 | 154 |
| " | 2.0 | 275 |
| Compound C | 5.0 | 171 |
| " | 10.0 | 283 |
| Compound D | 5.0 | 138 |
| " | 10.0 | 183 |
| Compound E | 10.0 | 175 |
| " | 20.0 | 206 |
| furosemide | 5.0 | 113 |
| " | 10.0 | 188 |

TABLE 1-continued

| Test Compound | Dose, mg/kg | Diuretic Activity, % |
|---|---|---|
| " | 20.0 | 292 |
| triamterene | 10.0 | 192 |
| " | 20.0 | 242 |

It is apparent from Table 1 that each of the compounds according to the present invention has an effective diuretic activity and superior to commercially available diuretics in diuretic activity.

EXPERIMENT 2

Hypertensive Action in Rats

A suspension of the test compound in a 5% arabic gum solution was orally to rats catheterized before more than 24 hours according to Mizokami et al. (Nihon Taishitsugaku Zasshi, 32, p.p. 59–63 (1969)). The blood pressures of the tested rats were measured without anesthesia and immersion and shown in Table 2.

TABLE 2

| | | Variation in Blood Pressures | |
|---|---|---|---|
| Test Compound | Dose, mg/kg | Percentage Increase | Duration Period (min.) |
| Compound A | 1 | 49 | 55 |
| Compound B | 2 | 42 | 65 |
| Compound C | 5 | 40 | 70 |
| Compound D | 5 | 35 | 50 |
| Compound E | 10 | 52 | 85 |

It was found that each of the test compounds acted as increasing the blood pressures of the test rats.

EXPERIMENT 3

Cardiotropic Action in Isolated Guinea-Pig Atria

The isolated atria from male Guinea-Pigs weighing about 350 grams were hanged in an organ bath filled with a Krebs-Henselite's solution and bubbled with a mixed gas (5% $CO_2$ and 95% $O_2$) at 30° C. A solution of the test compound in dimethylsulfoxide was added to the bath. The contractile force and beats were then measured and calibrated into a percentage increase of the contractile force and a percentage decrease of the beats. The results are shown in Table 3.

TABLE 3

| Test Compound | Concentration μg/ml | Percentage Increase of Contractile Force (%) | Percentage Decrease in Beats (%) |
|---|---|---|---|
| Compound A | 1 | 15.4 | 5.4 |
| Compound B | 1 | 11.5 | 2.3 |
| Compound C | 3 | 7.4 | 4.2 |
| Compound D | 3 | 6.9 | 3.6 |
| Compound E | 10 | 5.7 | 2.2 |

It is shown from Table 3 that the test compounds exhibited each an increasing contractile force and a decreasing beats of atria, thereby achieving the cardiotropic action.

EXPERIMENT 4

Therapeutic Action on Hyperemia of Rabbit Eye Mucosa

100 μl of 0.03 N sodium hydroxide was instillated into one eye to induce hyperemia in male Japanese albino rabbits weighting about 3 Kg. A group of 3 rabbits was used for test, which were caused an erythema score 1 on their conjunctive based on the standards of Fukui and Ikemoto (Gendai-no-Rinshao, 4, pp. 277 (1970)). The test compound was dissolved in a 10% NIKKOL HCO-60 (trademark: Nikko Chemical Co., Ltd.) and instilled to the test rabbit at a rate of 50 μl. The therapeutic activity was determined and shown in Table 4.

TABLE 4

| Test Compound | Concentration (%) | Average Erythema Score | |
| --- | --- | --- | --- |
| | | Before Treatment | After Treatment |
| Solvent alone | — | 1 | 1 |
| Compound A | 0.05 | 1 | 0.33 |
| Compound B | 0.05 | 1 | 0.33 |
| Compound C | 0.2 | 1 | 0.33 |
| Compound D | 0.2 | 1 | 0.5 |
| Compound E | 0.1 | 1 | 0.5 |

It is shown from Table 4 that each of the test compounds exhibited the therapeutic effect on the mucosal hyperemia.

EXPERIMENT 5

Acute toxicity

A group of 10 male mice of ddY strain weighing about 25 grams was administered orally or intraperitoneally with a suspension of the test compound in a 5% arabic gum solution in the amount of 10 ml per kg. of body weight. The LD$_{50}$ values were calculated by means of the Wilcoxon-Litchfield method on the number of mice died for seven days after administration. The results are shown in Table 6.

TABLE 5

| Test Compound | LD$_{50}$ values (mg/kg) | |
| --- | --- | --- |
| | Orally | i.p. |
| Compound A | 1,280 | 795 |
| Compound B | 462 | 322 |
| Compound C | >1,500 | >1,000 |
| Compound D | >1,500 | >1,000 |
| Compound E | 1,010 | 630 |

It is apparent from the above results that the azo compound according to the present invention possesses diuretic, hypertensive and cardiotropic activities, and is effective for mucosal hyperemia. The azo compound is extremely low in toxicity. It is accordingly shown that the azo compound are effective for the treatment of edema, hypotension, cardiac insufficiency and hyperemia in mammals.

What is claimed is:

1. A method of treating edema comprising administering to a patient suffering therefrom a fluid reducing effective amount of a compound of the formula

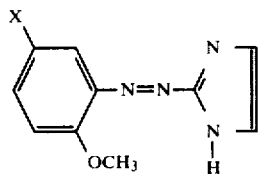

wherein X is hydrogen or halogen, or a pharmaceutically acceptable salt thereof.

2. A method of treating hypotension comprising administering to a patient suffering therefrom a blood pressure increasing effective amount of a compound of the formula

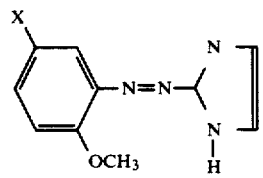

wherein X is hydrogen or halogen, or a pharmaceutically acceptable salt thereof.

3. A method of treating cardiac insufficiency comprising administering to a patient suffering therefrom a cardiac regulating effective amount of a compound of the formula

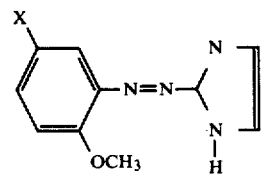

wherein X is hydrogen or halogen, or a pharmaceutically acceptable salt thereof.

4. A method of treating hyperemia comprising administering to a patient suffering therefrom a fluid reducing effective amount of a compound of the formula

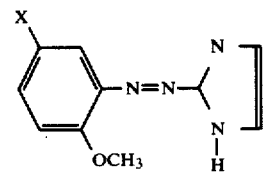

wherein X is hydrogen or halogen, or a pharmaceutically acceptable salt thereof.

5. The method of claim 1 or 4 wherein said compound is administered in an amount of about 0.01 to about 1,000 mg.

6. The method of claim 1 or 4, wherein said pharmaceutically acceptable salt is an inorganic acid addition salt or an organic acid addition salt.

* * * * *